Figures 1A, 1B:
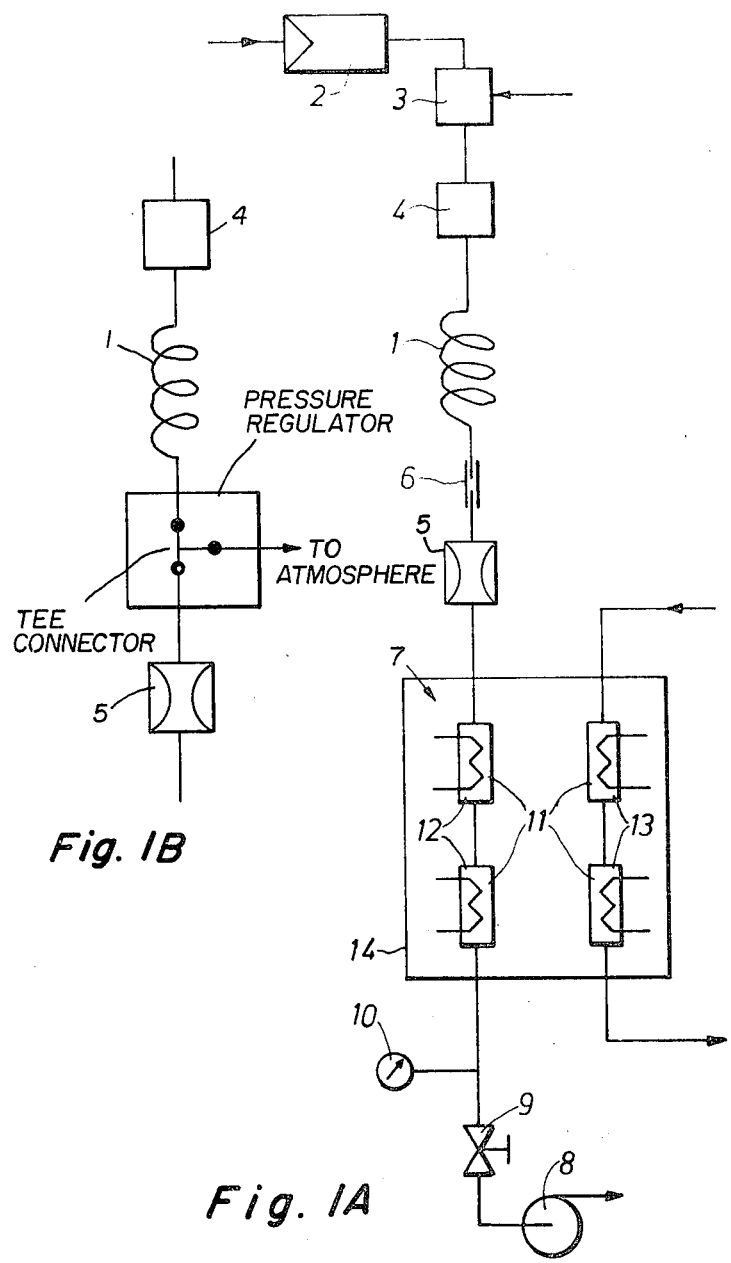

United States Patent [19]

Schirrmeister

[11] 4,151,741

[45] May 1, 1979

[54] METHOD AND APPARATUS FOR GAS CHROMATOGRAPHIC ANALYSIS

[75] Inventor: Horst Schirrmeister, Dormagen, Fed. Rep. of Germany

[73] Assignee: Bayer Aktiengesellschaft, Leverkusen, Fed. Rep. of Germany

[21] Appl. No.: 814,755

[22] Filed: Jul. 11, 1977

[30] Foreign Application Priority Data

Jul. 24, 1976 [DE] Fed. Rep. of Germany ....... 2633337

[51] Int. Cl.$^2$ ............................................. G01N 31/08
[52] U.S. Cl. ..................................................... 73/23.1
[58] Field of Search .............................. 73/23.1, 27 R; 23/232 C, 254 R

[56] References Cited

U.S. PATENT DOCUMENTS

| | | | |
|---|---|---|---|
| 2,920,478 | 1/1960 | Golay | 73/23.1 |
| 3,240,052 | 3/1966 | Reinecke et al. | 73/23.1 |
| 3,483,731 | 12/1969 | Sanford et al. | 73/23.1 |
| 3,905,222 | 9/1975 | Boillot | 73/19 |

FOREIGN PATENT DOCUMENTS 1122293  1/1962  Fed. Rep. of Germany ............ 73/23.1

OTHER PUBLICATIONS

Ettre et al., "Investigation of Linearity of Stream Splitter for Capillary Gas Chrom.", *Analytical Chemistry*, vol. 33, No. 6, pp. 680–684, May 1961.

Wilhite, "Developments in Micro Gas Chrom.", *Journal of Gas Chrom.*, pp. 47–50, Feb. 1966.

*Primary Examiner*—Stephen A. Kreitman
*Attorney, Agent, or Firm*—Sprung, Felfe, Horn, Lynch & Kramer

[57] ABSTRACT

An improvement in the resolution, sensitivity of measurement and sensitivity of detection in gas chromatographic analysis using a capillary column or micropacked column as a separating column and a thermal conductivity cell as a detector wherein the pressure in the gas chamber at the beginning of the separating column is higher than in the detector by a factor of at least 5.

10 Claims, 4 Drawing Figures

METHOD AND APPARATUS FOR GAS CHROMATOGRAPHIC ANALYSIS

This invention relates to a method and to an apparatus for gas chromatographic analysis with a capillary column or micropacked column as a separating column and a thermal conductivity cell as a detector.

It is known to use capillary columns or micropacked columns of metal or glass in gas chromatographic analysis. These columns have a higher separation efficiency than conventionally packed columns but they make special demands on the detector because they can only be charged with relatively small quantities of samples. The instruments used for measuring concentration in gas chromatography are thermal conductivity cells. They are easy to handle and their sensitivity is not unduly dependent on the nature of the substance under investigation. When concentration measurements are carried out with a thermal conductivity cell, it is essential that the volume of the thermal conductivity cell be completely filled with the mixture under investigation. In capillary columns or micropacked columns, the volume of the stream of carrier gas which contains the components to be detected is generally smaller than the volume of a thermal conductivity cell so that one characteristic of capillary columns or micropacked columns, namely their narrow peak range, cannot be fully utilised because the thermal conductivity cell is not optimally suited as a detector. It is in many cases impossible to use flame ionisation detectors instead of thermal conductivity cells because they are numerous substances which are not indicated by flame ionisation detectors and in every case it is necessary to know the calibration factors, which vary from one substance to another. Special models of thermal conductivity cells with exceptionally small volume have a lower sensitivity of measurement (Methoden der Analyse in der Chemie, Volume 14, D. Jentzsch, E. Otte, Dektoren in der Gaschromatographie, Akademische Verlagsgesellschaft, 1970).

It is also known to carry out gas chromatography at subatmospheric pressures. At pressures below 200 mbar, both the sensitivity and the speed of analysis are higher. For this reason, both separating columns and detectors have been operated at lower than atmospheric pressure (D. C. Locke, W. W. Brand, Reduced Pressure Gas Chromatography, Gas Chromatography 1963, 55-76). However, such operation at reduced pressure does not obviate the disproportionate relationship between the small volume of the stream of carrier gas containing the component to be detected and the much larger volume of the thermal conductivity cell.

It is an object of the present invention to increase the resolution, sensitivity of measurement and sensitivity of detection in gas chromatographic analysis. It is particularly intended that the improved sharpness of separation obtained by using capillary columns or micropacked columns should not be diminished by the detection. It is also intended that concentrations should be easily measured.

According to the invention, there is provided a method of gas chromatographic analysis wherein the separating column comprises a capillary column or a micropacked column and the detector comprises a thermal conductivity cell, and wherein the pressure of the gas immediately upstream of the separating column is higher than that in the detector by a factor of at least five.

There is also provided an apparatus for gas chromatographic analysis, comprising a capillary column or micropacked column as the separating column and a thermal conductivity cell as a detector and a constriction arranged between the detector and the separating column.

The pressure conditions in the column and the detector are described in more detail below.

The pressure in the gas stream in the separating column should be higher than that in the thermal conductivity cell by a factor of at least 5. Even in conventionally packed columns this condition is not disadvantageous but the gain in sharpness of separation is not so obvious. The factor for the pressure ratio between column and detector is most preferably between 10 and 1000.

It is advisable to maintain a pressure of between 0.1 and 500 mbar in the thermal conductivity cell and a pressure range of between 0.5 and 200 mbar is particularly preferred.

To ensure that the pressure in the thermal conductivity cell will not fall below a minimum pressure, i.e. to ensure that the mean free path of the gas molecules inside the thermal conductivity cell remains smaller than the dimensions of the thermal conductivity cell, it may be necessary to arrange a constriction between the vacuum pump and the cell. A constriction arranged in this position is also suitable for keeping the pressure in the cell constant since it protects the cell from fluctuations in the pump output.

The pressure at the outlet of the separating column and upstream of the constriction is preferably atmospheric pressure. When the operating conditions in the chromatograph are adjusted so that the pressure upstream of the constriction is atmospheric pressure, the operating conditions coincide with those commonly used in gas chromatography, where the most extensive experience is available and no conversions or recalibrations are necessary.

A connection to the atmosphere or to a pressure regulated container may be provided downstream of the separating column in order to keep the pressure upstream of the constriction constant. The flow through the column and through the detector are thereby to a large extent separated. The arrangement is operated so that slightly more gas flows through the separating column than is removed by suction through the constriction.

Since the flow conditions through the constrictions which determine the pressure in the measuring cell are dependent upon the temperature, it may be necessary to keep the constrictions at a constant temperature.

The volume of the mixture of gases to be measured increases by the same factor as the pressure change across the constriction between the column and the thermal conductivity cell. It is therefore possible to combine thermal conductivity cells of the usual dimensions with gas chromatographs comprising capillary columns or micropacked columns. Resolution, sensitivity of measurement and sensitivity of detection are just as great as under normal pressure for a given concentration of components in the eluate, provided that the measuring cell is completley filled at normal pressure. The pressure conditions in the separating column and in the thermal conductivity cell are to a large extent rendered independent of each other by the constriction.

As a first approximation, the rate of flow depends only on the bias pressure and not on the much lower pressure downstream of the constriction. The constriction is so designed that it will admit a suitable rate of flow (dependent upon the bias pressure) for gas chromatographic separation.

Dead volumes, variations in cross-section and absorbent deposits downstream of the constriction now have virtually no deleterious effects. The supply of an accelerating gas (commonly used when working with flame ionisation detectors) can be dispensed with.

Due to the reduction of pressure in the measuring cell, the cell housing may be kept at a lower temperature than that used at normal pressure without any risk of condensation of components of the sample. This results in an even greater sensitivity of measurement since the measuring sensitivity of thermal conductivity detectors increase with the temperature difference between the detector element (for example the hot wire) and the housing. This increase in sensitivity is obtained quite independently of any improvement in the detection of small quantities and may also be used to advantage when packed columns are employed. If the possibility of using a lower cell housing temperature is not intended to be utilised for obtaining a higher sensitivity of measurement, it is possible to keep the detector element (for example the hot wire) at a lower temperature, thereby reducing the corrosion which occurs in some cases and increasing the life of the detector.

When the apparatus according to the invention is used, thermal conductivity cells of the usual dimensions are capable of analysing the streams of gas eluted from capillary columns or micropacked columns with the same resolution, sensitivity of measurement and limits of detection as can be achieved at normal pressure with the same concentrations of components in the eluate if the volumetric flow is greater by the factor of the pressure reduction.

In the simplest case, the constriction is formed by the compression of a metal tube. However, there is no difficulty in installing calibrated constrictions such as microslits or calibrated capillaries. A needle valve may be used as the constriction between the thermal conductivity cell and the vacuum pump.

It is advantageous to monitor the pressure in the thermal conductivity cell.

Figure 2:
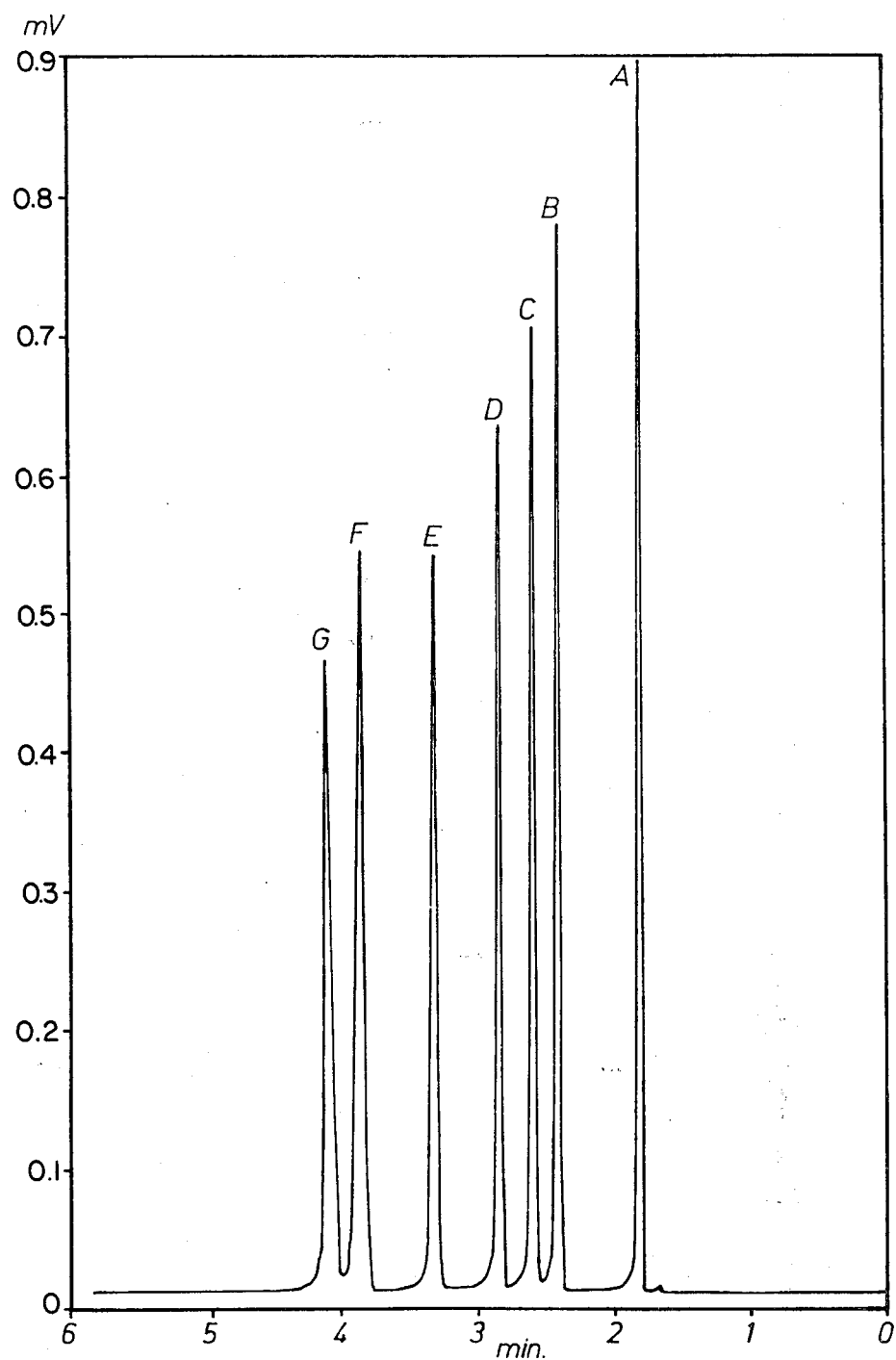
Figure 3:
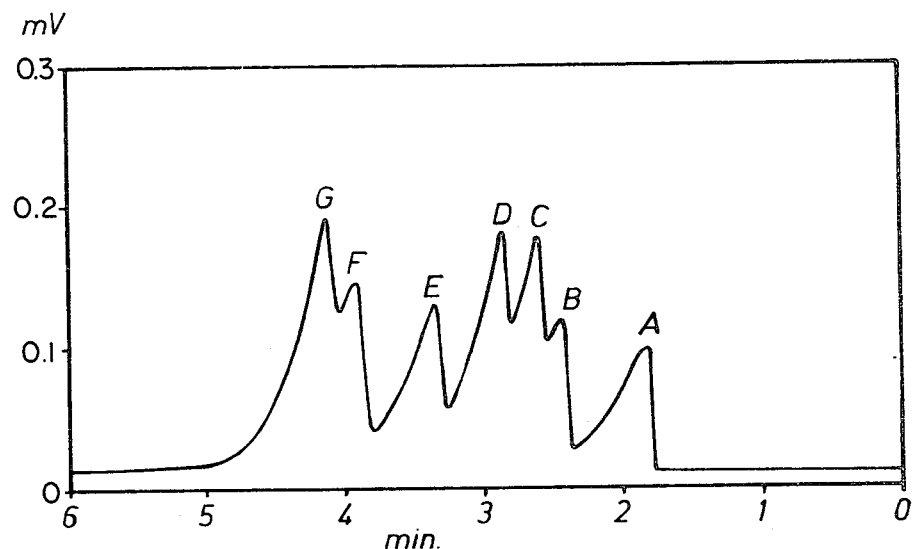

An apparatus according to the invention is described below with reference to the drawings in which FIG. 1A is a circuit diagram of the apparatus, FIG. 1B is a circuit diagram of a detail of an alternate embodiment of FIG. 1A, FIG. 2 is a chromatogram obtained with the apparatus according to the invention and FIG. 3 is a chromatogram obtained with conventional apparatus.

As shown in FIG. 1A, the gas chromatographic separating column 1 is a glass capillary 18 meters in length and 0.25 mm in internal diameter lined with silicone oil. The bias pressure is adjusted at 2 so that gas flows through the column at the rate of 1.8 ml/min at room temperature. The absolute pressure at the outlet of the column is one bar. The sample to be analysed is introduced through the injection unit 3. The input divider 4 reduces the quantity of sample flowing through the column to a fraction. The constriction 5 is formed by a squashed steel capillary 0.2 mm in internal diameter connected to the column 1 by a shrunk-on Teflon sleeve 6. The resistance of the constriction 5 is regulated experimentally by connecting a vacuum pump to the constriction and increasing the constriction until at a pressure difference of approximately 1 bar the rate of flow through the constriction is 1.8 ml/min, measured with a soap bubble meter. The thermal conductivity cell 7 is connected to the constriction 5. A second constriction 9 in the form of a needle valve is provided between the cell 7 and the vacuum pump 8. The thermal conductivity cell is maintained at a pressure of 20 mbar, which can be monitored with a manometer 10. The vacuum pump 8 has a suction output of 6m³/hour. A model 417 gas chromatograph of Packard Instruments is used. Each of the four thermal conductivity cells 11 has a volume of 0.4 ml. The measuring gas stream in the two cells 12 is at a pressure of 20 mbar. Helium flows at normal pressure through the two cells 13 of the comparison systems. The bridge current is 100 mA. Under these operating conditions, the temperature of the heating wires in the cells 12 is about 5% higher than in the cells 13. The temperature of the heated housing unit 14 of the thermal conductivity cells is 130°. Under these conditions, the bridge can be balanced with the built-in resistors.

FIG. 1B shows an alternative embodiment wherein a pressure regulator including a tee connector device has one side connected to the column, the second side connected to the constriction valve and the third side opened to the atmosphere.

A chromatogram obtained with this apparatus is shown in FIG. 2. The injected sample contains the following components:

A n-pentane
B 2-methylpentane
C 3-methylpentane
D n-hexane
E methyl cyclopentane
F benzene
G cycolhexane.

0.8 μl are injected into the injection unit 3 heated to 150° C. The input divider 4 reduces the quantity of sample to 1/150 in order to prevent overloading of the capillary column. The signal of the detector is reduced to 1:8. The full excursion of the writing instrument is 1 mV.

A chromatogram obtained with a conventional chromatograph is shown as a comparison example in FIG. 3. The composition of the mixture, the flow conditions through the column, the quantity injected, the reduction ratio of the input divider, and the sensitivity setting of the thermal conductivity cell or of the recording instrument are unchanged. Only the constriction 5 and the vacuum equipment required in this example are absent.

What we claim is:

1. In a method of gas chromatographic analysis wherein the improvement comprises providing a separating column comprising one of a capillary column or micropacked column and a detector comprising a thermal conductivity cell, and maintaining the absolute pressure of the gas immediately upstream of the separating column higher than that in the detector by a factor of at least five by providing a constriction after the separating column and before the detector.

2. A method as claimed in claim 1, further comprising maintaining the pressure of the gas at the outlet of the separating column substantially constant.

3. A method as claimed in claim 2, wherein the pressure of the gas at the outlet of the separating column is substantially atmospheric pressure.

4. A method as claimed in claim 1, further comprising removing gas from the thermal conductivity cell by a vacuum pump and providing a constriction between the vacuum pump and the thermal conductivity cell.

5. A method as claimed in claim 4, wherein an absolute pressure of from 0.5 to 200 mbar is maintained in the thermal conductivity cell by the constrictions arranged before and after the thermal conductivity cell and the pressure at the outlet of the separating column is substantially atmospheric pressure.

6. An apparatus for gas chromatographic analysis, comprising a separating column comprising one of a capillary column or micropacked column, a detector comprising a thermal conductivity cell and means for maintaining the absolute pressure of the gas in the detector lower by a factor of at least five than the absolute pressure of the gas at the outlet of the separating column, comprising a constriction disposed after the separating column and before the detector.

7. An apparatus as claimed in claim 6, further comprising regulating means in communication between the constricton and the separating column to maintain the pressure of the gas at the outlet of the separating column substantially constant.

8. An apparatus as claimed in claim 7, further comprising a vacuum pump connected to the thermal conductivity cell via a further constriction.

9. An apparatus according to claim 7, wherein the regulating means comprises a communication to atmospheric pressure.

10. The apparatus according to claim 7, wherein the regulating means maintains the outlet pressure of the separating column at substantially atmospheric pressure, and comprises a tee-connector disposed between the column and the constriction and having a connection to the atmosphere and wherein the detector maintains a pressure of from 0.5 to 200 mbar.

* * * * *